United States Patent [19]
Sachdeva et al.

[11] Patent Number: 6,054,598
[45] Date of Patent: Apr. 25, 2000

[54] SYNTHESIS OF 2-ALKOXYESTRADIOLS

[75] Inventors: Yesh Sachdeva, Concord; Siya Ram, Winchester, both of Mass.

[73] Assignee: Pharm-Eco Laboratories, Inc., Lexington, Mass.

[21] Appl. No.: 09/046,362

[22] Filed: Mar. 23, 1998

Related U.S. Application Data

[62] Division of application No. 08/816,558, Mar. 13, 1997.

[51] Int. Cl.[7] ...................................................... C07J 1/00
[52] U.S. Cl. .......................................................... 552/627
[58] Field of Search ..................................... 552/614, 627

[56] References Cited

U.S. PATENT DOCUMENTS 5,405,944  4/1995  Suzuki et al. ............................... 536/5

OTHER PUBLICATIONS

Slaunwhite et al., "Bromination of phenolic steroid. I. Substitution of estrone and 17beta–estradiol in ring A". J. Org. Chem. vol. 27, pp. 1749–1752, 1962.

He et al., "A versatile synthesis of 2–methoxyestradiol, an endogenous metabolite of estradiol which inhibits tubulin polymerization by binding to the colchicine binding site", Biorganic & Medicinal Chem. Lett. vol. 4(14), pp. 1725–1728, 1994.

Chen et al., "A New synthetic route 2–and 4–methoxyestradiols by nucleophilic substitution". Steroids, vol. 47(1), pp. 63–66, 1986.

Pert et al., "An alternative route to 2–bromo and 2–iodo–estradiols from estradiol". Aust. J. Chem., vol. 40, pp. 303–309, 1987.

Rao et al., "A novel, two–step synthesis of 2–methoxyestradiol". Synthesis, pp. 168–169, 1977.

D. J. Pert and D. D. Ridley, "Formylation of Oestrogens," Aust. J. Chem., 42:405–19 (1989).

S. Chen, et al., "A New Synthetic Route to 2–and 4–Methoxyestradiols by Nucleophilic Substitution," Steroids 47 (1) :63–66 (Jan. 1986).

P. N. Rao and J. E. Burdett, Jr., "Novel Two–Step Synthesis of 2–Methoxyestradiol," Synthesis, pp. 168–169 (Mar. 1977).

H. M. He, et al., "A Novel 1,3 O→C Silyl and Deacylation Reaction Mediated by Tetra–n–butylammonium Fluoride in an Aromatic System," J. Org. Chem., 60:5905–5909 (1995).

W. R. Slaunwhite, Jr., and L. Neeley, Bromination of Phenolic Steroids. I. Substitution of Estrone and 17β–Estradiol in Ring A[1] Bromination of Phenolic Steroids I, J. Org. Chem. 27:1749–1752 (1962).

M. Cushman, et al., "Synthesis, Antitubulin and Antimitotic Activity, and Cytotoxicity of Analogs of 2–Methoxyestradiol, an Endogenous Mammalian Metabolite of Estradiol that Inhibits Tubulin Polymerization by Binding to the Colchicine Binding Site," J. Med. Chem. 38:2041–2049 (1995).

H. M. He and M. Cushman, "A Versatile Synthesis of 2–Methoxyestradiol, An Endogenous Metabolite of Estradiol which Inhibits Tubulin Polymerization by Binding to the Colchicine Binding Site," Biorganic & Medicinal Chemistry Letters, 4(14) :1725–1728 (1994).

Cushman, M., et al., "Synthesis of Analogs of 2–Methoxyestradiol with Enhanced Inhibitory Effects on Tubulin Polymerization and Cancer Cell Growth," J. Med. Chem. 40:2323–2334 (1997).

Numazawa, M. et al., "Synthesis of 2–Methoxy–and 4–Methoxy–Estrogens with Halogen–Methoxy Exchange Reaction," J. Chem. Res. Miniprint 11:3701–3715, Paper E/155/85 (Dec. 31, 1984).

Nambara, T., et al. "Studies on Steroid Conjugates. III. New Synthesis of 2–Methoxyestrogens," Chem. Pharm. Bull. 18 (3) :474–480 (1970).

Zheng, X–h, et al., "A New Synthetic Route to Pyrogallolestrogen Dimethyl Ethers by Nucleophilic Substitution of 2,4–Dibromoestrogens," Steroids 40 (2) :121–124 (1982).

Horiuchi, C.A., et al., "Novel Regioselective Iodination of Estradiol 17β–Acetate," Bull. Chem. Soc. Jpn. 59(8) :2459–2462 (1986).

Primary Examiner—Jose' G. Dees
Assistant Examiner—Barbara Badio
Attorney, Agent, or Firm—Hamilton, Brook, Smith & Reynolds, P.C.

[57] ABSTRACT

Disclosed is a method of preparing a compound represented by the following structural formula:

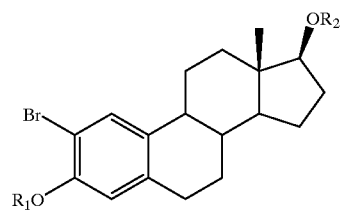

The method comprises reacting bromine ($Br_2$) and an aliphatic organic acid with a compound represented by the following structural formula:

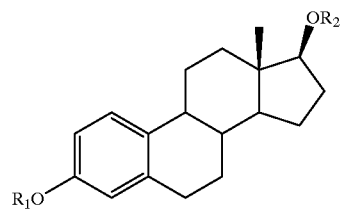

$R_1$ and $R_2$ are each independently a hydroxyl protecting group.

5 Claims, 1 Drawing Sheet

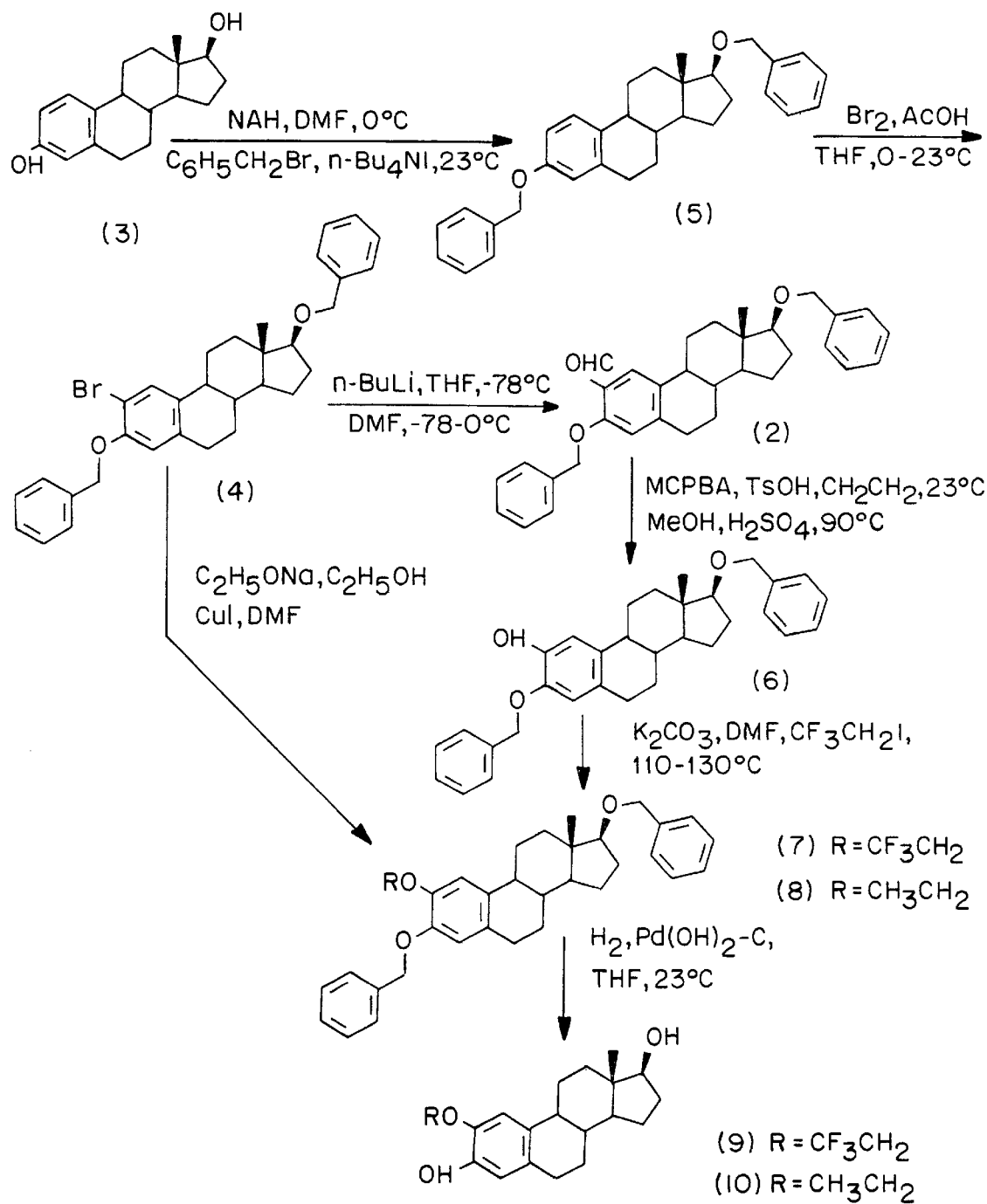

SYNTHESIS OF 2-ALKOXYESTRADIOLS

RELATED APPLICATION

This application is a Divisional Application of U.S. Patent Application No. 08/816,558 filed on Mar. 13, 1997, the entire teachings of which are incorporated herein by reference.

GOVERNMENT SUPPORT

This invention was made with government support under National Cancer Institute Contract No. NOI-CM-27764. The government has certain rights in the invention.

BACKGROUND OF THE INVENTION

At least some 2-alkoxy-estra-3,17β-diols (hereinafter "2-alkoxy estradiols") have anticancer activity. For example, when tested in mice, 2-methoxy estradiol (1) acts as a potent inhibitor of neovascularization of solid tumors and inhibits their growth at doses which produce no apparent signs of toxicity (Fotsis et al., *Nature* 368:237 (1994)). Other 2-alkoxy estradiols that are believed to have anti-cancer activity are disclosed in co-pending U.S. provisional patent application "Novel 2-Alkoxy Estradiols and Derivatives Thereof", filed on Mar. 13, 1997 (Attorney Docket No. PEL95-15p). 2-Methoxy estradiol (1) is thought to inhibit tumor growth act by: 1) inhibiting DNA synthesis and mitosis (Breuer et al., Naturwissenschaft 12:280 (1960) and Gelbke et al., *J. Steroid Piochem*, 7:457 (1976)); 2) inhibiting tubulin polymerization or causing the formation of tubulin polymer with altered morphology and stability properties (D'Amato et al., *Proc. Natl. Acad. Sci. U.S.A.*

(1)

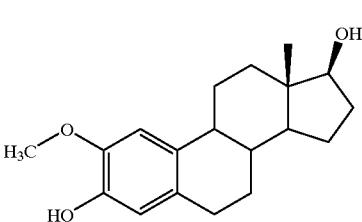

91:3964 (1994)); or 3) inhibiting angiogenesis, i.e. the creation of new blood vessels required for the growth of solid tumors (Fotsis et al., *Nature* 368:237 (1994), Folkman et al., *Nature* 339:58 (1994) and Blood et al., *Biochim. Biophys. Acts* et al., 1032:89 (1990)).

Syntheses previously employed to prepare 2-alkoxy estradiols have often suffered from low yields and a need to utilize tedious purification techniques. For example, one reported synthesis of 2-methoxy estradiol (1) involves the preparation of 2-formyl-β-estradiol dibenzyl ether (2)

(2)

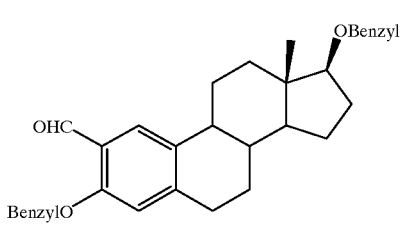

(3)

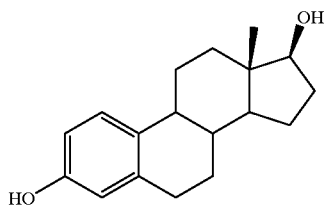

as a key intermediate by formylation of β-estradiol (3), followed by benzylation of the two hydroxyl groups (Cushman et al., *J. Med. Chem.* 38:2041 (1995)). However, yields less than 10% are typically obtained from the two reactions. In addition, because the formylation reaction gives a mixture of regioisomers, 2-formyl-β-estradiol dibenzyl ether (2) must be purified by chromatography, which is generally considered to be an inefficient method of purification for large scale syntheses.

Therefore, a need exists for a method of synthesizing 2-alkoxy estradiols that overcomes or minimizes the above-mentioned problems.

SUMMARY OF THE INVENTION

The present invention is directed to an improved method for synthesizing 2-alkoxy estradiols and to specific 2-alkoxy estradiols. The invention is also directed to improved methods for preparing intermediates useful in the preparation of 2-alkoxy estradiols.

One embodiment of the present invention is a method of preparing a compound represented by the following structural formula:

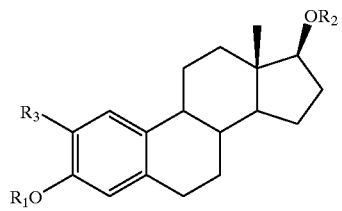

The method comprises reacting bromine ($Br_2$) or iodine ($I_2$) and an aliphatic organic acid with a compound represented by the following structural formula:

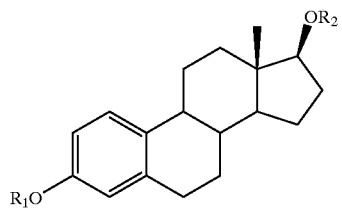

$R_1$ and $R_2$ are each independently a hydroxyl protecting group. Preferably $R_1$ and $R_2$ are each a benzyl or substituted benzyl group, more preferably a benzyl group. $R_3$ is —Br or —I.

The organic acid is preferably a C1 to C5 aliphatic organic acid, preferably a C1–C5 aliphatic carboxylic acid, more preferably acetic acid.

Yet another embodiment of the present invention is a method of preparing a compound represented by the following structural formula:

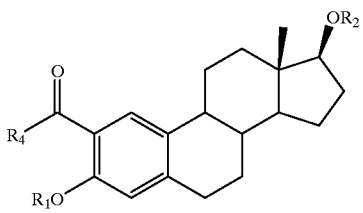

$R_1$ and $R_2$ are as described above. $R_4$ is selected from the group consisting of —H. a lower alkyl group and a substituted lower alkyl group. $R_4$ is preferably —H.

The method comprises reacting an organolithium reagent and a synthetic equivalent of $R_4CO^+$ with a compound represent by the following structural formula:

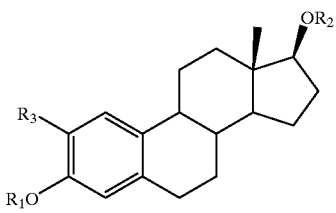

$R_1$–$R_4$ are as described above. The organolithium reagent is preferably n-butyllithium. The synthetic equivalent of $R_4CO^+$ is preferably dimethylformamide.

Another embodiment of the present invention is a compound represented by the following structural formula:

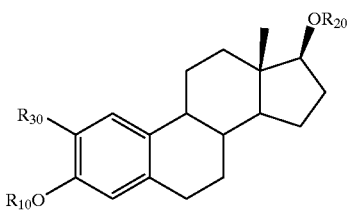

$R_{10}$ and $R_{20}$ are independently a benzyl group or a substituted benzyl group. Preferably, $R_{10}$ and $R_{20}$ are each a benzyl group. $R_{30}$ is —Br or —I.

The present invention has many advantages. For example, the bromination and the halogen-metal exchange reactions disclosed herein can be used to prepare 2-formyl-β-estradiol dibenzyl ether (2) in higher overall yields than known methods. In addition, the bromination introduces bromine predominantly at the two position of β-estradiol dibenzyl ether (5) to give a novel brominated estradiol dibenzyl ether intermediate (4), which can be substantially purified by crystallization. Thus, the disclosed method of preparing 2-formyl-β-estradiol dibenzyl ether (2) provides higher yields than methods previously used to prepare this compound with decreased formation of the 4-bromo by-product. As noted above, 2-formyl-β-estradiol dibenzyl ether (2) is an intermediate in the synthesis of 2-alkoxy-β-estradiols. Using the method of the present invention, 2-alkoxy estradiols can be synthesized more economically and in higher overall yield than was previously possible.

BRIEF DESCRIPTION OF THE DRAWING

The FIGURE is a schematic representation of the synthesis of 2-alkoxy estradiols.

DETAILED DESCRIPTION OF THE INVENTION

The features and details of the invention will now be more particularly described below and pointed out in the claims. It will be understood that the particular embodiments of the invention are shown by way of illustration and not as limitations of the invention. The principal features of this invention can be employed in various embodiments without desparating from the scope of the invention.

2-Alkoxy estradiols and a numbering system for identifying each carbon atom in the estradiol ring system are shown in the following structural formula:

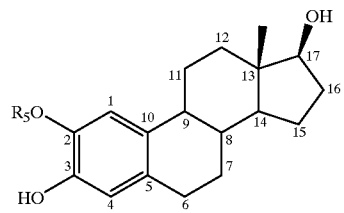

$R^5$ is a lower alkyl group or a substituted lower alkyl group.

As used herein, suitable lower alkyl groups include C1–C6 straight or branched chain hydrocarbons which can optionally contain one or more double or triple bonds.

Suitable substituent on a lower alkyl group or phenyl group include one or more halogens (e.g., fluoro, chloro, bromo and iodo), nitro, nitrile, —NH$_2$, —NH(lower alkyl), —NH (substituted lower alkyl), —N(lower alkyl)$_2$, —N(substituted lower alkyl), carbonyl groups, —CONH$_2$, —CONH(lower alkyl), —CONH(substituted lower alkyl), —CON(lower alkyl)$_2$, —CON(substituted lower alkyl)$_2$, —CO$_2$H, —COO(lower alkyl) and —COO(substituted lower alkyl). Halogenated alkyl groups can contain more than one kind of halogen. Examples of suitable lower alkyl or substituted lower alkyl groups include methyl, ethyl, n-propyl, isopropyl, trifluoromethyl, trifluoroethyl, NO$_2$—CH$_2$—CH$_2$ —,(CH$_3$)$_2$ N—CH$_2$—CH$_2$—, —CH$_2$CH$_2$—CO—R', wherein $R_1$ is —H, lower alkyl, substituted lower alkyl, —OH, —O lower alkyl), —O(substituted lower alkyl), —NH, —NH(lower alkyl), —NH (substituted lower alkyl), —N(substituted lower alkyl)$_2$ and —N(lower alkyl)$_2$.

Using the bromination and metallation reactions of the present invention, 2-alkoxy estradiols can be prepared from estradiol (3). The FIGURE shows schematically the preparation of 2-ethoxy estradiol (10) and 2-(2',2',2'-trifluoroethoxy)estradiol (9) by this synthesis. Each of the reactions in this synthesis is described in greater detail below.

A first intermediate is prepared from estradiol (3) by protecting the two hydroxyl groups to form a compound represented by Structural Formula (I):

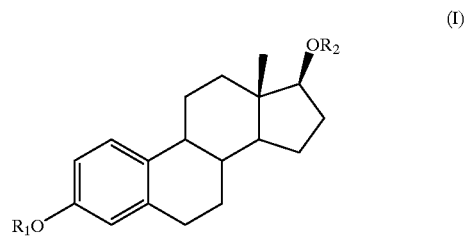

$R_1$ and $R_2$ are each independently a hydroxyl protecting group. Preferably $R_1$ and $R_2$ are each a benzyl or substituted benzyl group, more preferably a benzyl group.

As used herein, hydroxyl refers to alcohols and phenolic groups. A "suitable protecting group" is substantially inert with respect to the reagents used in the subsequent reactions in the disclosed synthesis of 2-alkoxy estradiols and does not cause, for example, undesired side reactions. Hydroxyl protecting groups are well known in the art and are described in, for example, Chapters 2 and 3 of Greene and Wuts, "Protective Groups in Organic Synthesis", John Wiley & Sons (1991), the entire teachings of which are incorporated into this application by reference. The skilled artisan can select, using no more than routine experimentation, suitable groups for use in the disclosed synthesis as well as conditions for applying and removing the hydroxyl protecting groups.

Preferred hydroxyl protecting groups include benzyl groups and substituted benzyl groups. Examples of suitable substituents for benzyl protecting groups include, but are not limited to, one or more of the following groups: lower alkyl, fluoro, chloro, (lower alkyl)-O—, nitro, phenyl, di(lower alkyl)aminocarbonyl and silyl. Protecting a free hydroxyl group with a benzyl group or substituted benzyl group is referred to herein as "benzylating" the hydroxyl group.

Estradiols can be benzylated by reacting at least one equivalent of a benzyl chloride, bromide or iodide and at least one equivalent of a base per free hydroxyl group (see, for example, Venuti et al., J. Med. Chem. 31:2132 (1988)). Suitable bases include hydride bases such as sodium hydride, potassium hydride and lithium hydride. Typically, a molar excess of benzyl halide and sodium hydride are used with respect to each free hydroxyl group, for example up to a 1–3 fold excess of base and up to a 1–5 fold excess of benzyl halide. A catalytic amount of an iodide salt is preferably added to the reaction mixture, e.g., sodium iodide, potassium iodide or a tetraalkylammonium iodide. Suitable solvents include apolar diprotic solvents such as dimethylformamide, dimethyl sulfoxide and hexamethylphosphoramide. Suitable temperatures for carrying out the reaction range from about 0° C. to about 50° C., and preferably at room temperature. The starting material and base are preferably mixed at 0° C.

Methods of protecting a hydroxyl group are described in Greene and Wuts, pages 53–71 and 156–159) and are encompassed within the scope of this invention. Specific conditions for benzylating estradiol (3) are provided in Example 1.

The first intermediate is reacted with bromine ($Br_2$) or iodine ($I_2$) and an aliphatic organic acid in a suitable solvent to form a second intermediate represented by Structural Formula (II):

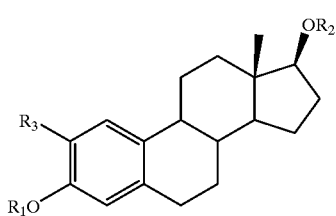

(II)

$R_1$ and $R_2$ are as described above. $R_3$ is —Br or —I.

Examples of suitable aliphatic organic acids include C1–C5 aliphatic carboxylic acids, sulfonic acids, sulfinic acids and phosphoric acids. Aliphatic carboxylic acids are preferred; acetic acid is particularly preferred.

The first intermediate is brominated (or iodinated) with at least one molar equivalent of bromine (or $I_2$) Typically an excess of bromine, for example up to about a three fold excess, can be used. Preferably, about a 10% to about a 20% excess of bromine is used. Suitable concentrations of bromine in the reaction mixture range, for example, from between about 0.01 M to about 5.0 M, and preferably between about 0.10 M and about 0.40 M.

Suitable solvents for the bromination reaction include, for example, etheral solvents in which the organic acid and estradiol are soluble, for example, tetrahydrofuran (THF), dioxane or glyme. THF is preferred. Suitable amounts of aliphatic organic acid include a volume/volume ratio of about 1:5 to about 5:1 with respect to the solvent, preferably about 3:2 with respect to tetrahydrofuran. The reaction can be run, for example, at temperatures between about −10° C. and about 45° C. Preferably, reagents are mixed under ice bath cooling, after which the reaction is allowed to warm to room temperature.

Specific conditions for brominating a first intermediate, specifically estra-3,17β-diol dibenzyl ether (5), are provided in Example 2. The bromination reaction using the conditions described above and in Example 2 forms predominently the 2-regioisomer over the 4-regioisomer. In addition, the brominated product can be substantially purified by crystallization from, for example, ethyl acetate.

The second intermediate is reacted with an organolithium reagent and a synthetic equivalent of $R_4CO^+$ to form a third intermediate represented by Structural Formula (III):

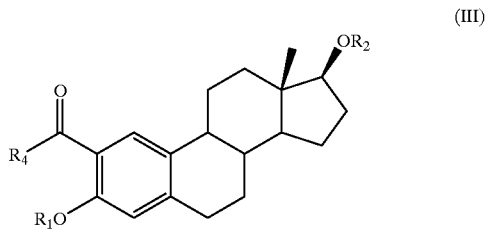

(III)

$R^1$ and $R^2$ are as described above. $R^4$ is selected from the group consisting of —H, lower alkyl and substituted lower alkyl.

Organolithium reagents are well known in the art and are described in Wakefield, "Organolithium Methods" Academic Press Limited, (1988), the teachings of which are incorporated herein by reference. Organolithium reagents are capable of reacting with aryl bromides and iodides such as bromobenzene to effect a halogen/lithium exchange to produce a lithiated intermediate, which can then be reacted with a suitable electrophile. This type of reaction is described in greater detail on pages 107–08 of Wakefield. Examples of suitable organolithium reagents include n-butyllithium, sec-butyllithium, t-butyllithium, methyllithium and lithium metal.

"Synthetic equivalent" has the meaning commonly associated with the term in the art of synthetic organic chemistry (see, for example, Warren, "Designing Organic Syntheses: A Programmed Introduction to the Synthon Approach", John Wiley & Sons, 1978, page 8, and March, "Advanced Organic Chemistry", John Wiley Sons, 1985, page 422, Corey, Pure Appl. Chem., 14:19 (1967) pages 20–23. "Synthetic equivalent" is understood to mean a reagent which functions as the equivalent of a structural unit in an organic molecule so that after one or more reactions with a precursor, the reagent adds that structural unit to the precursor. For example, dimethylformamide is a synthetic equivalent of $^+CHO$ and, under suitable conditions, reacts with nucleophiles, including lithiated intermediates, to add a —CHO moiety to the precursor. Thus, dimethylformamide achieves the same ultimate result as if a reagent which generated $^+$CHO directly were used. Suitable synthetic equivalents of $R_4CO^+$ include, for example, $R_4CO$—N (lower alkyl) (e.g., dimethylformamide), $R_4CO$—X, wherein X is a halide (e.g., acetyl chloride), —O—CO— (lower alkyl) (e.g., acetic anhydride) and —O—(lower alkyl) (e.g., ethyl acetate). Preferably, $R_4$ is —H and the synthetic equivalent of $R_4CO^+$ is dimethylformamide.

To produce the third intermediate, the second intermediate is typically reacted with, for example, between about 1.0 to about 5.0 equivalents, preferably between about 2.0 and about 3.0 equivalents, of an organolithium reagent, preferably n-butyllithium. Examples of suitable solvents include anhydrous etheral solvents (e.g., diethyl ether, dimethoxyethane, dioxane, tetrahydrofuran or diglyme) or anhydrous hydrocarbon solvents (e.g., benzene, pentane or hexane). THF is preferred. Suitable reaction temperatures range from, for example, between about –100° C. to to about –60° C., preferably between about –75° to about –85° C. Suitable concentrations of the second intermediate in the reaction mixture range between about 0.005 M to about 1.0 M, preferably between about 0.050 M to about 0.10 M. The temperature is maintained until halogen metal exchange is complete, from about ten minutes to about five hours, and typically about one to two hours, at which time an excess (e.g., from about 1.1 to about 10 fold, typically about 2.5 fold) of the synthetic equivalent of —$R_4CO^+$ with respect to organolithium reagent is added to the reaction mixture. The synthetic equivalent can be added neat or as a solution in an anhydrous etheral or hydrocarbon solvent. Typically, the reaction is warmed, for example, at about 0.5 to about 3.0 hours after addition of the synthetic equivalent to between about –30° C. to about room temperature, preferably about –10° C. to about 10° C., and allowed to stir until the reaction is complete. Specific conditions for converting a second intermediate, specifically 2-bromo-estra-3,17β-diol dibenzyl ether (4), to the third intermediate are provided in Example 3.

The third intermediate is reacted with an oxidizing agent capable of oxidizing an aryl alkyl ketone R—CO—Ar to the corresponding aryl alkonate R—CO—O—Ar to form a fourth intermediate represented by Structural Formula (IV):

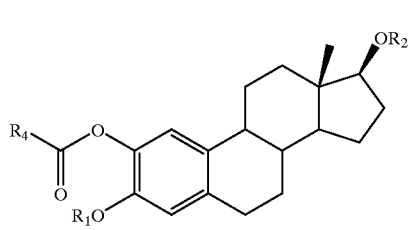

(IV)

The reaction of ketones or aldehydes in the presence of suitable oxidizing agents to give esters, as in the transformation of the third intermediate to the fourth intermediate, is commonly known in the field of organic chemistry as a "Baeyer-Williger Oxidation". This reaction is described, for example, in March, "Advanced Organic Chemistry", third edition, John Wiley & Sons, pages 990–91 (1985) and references cited therein, the teachings of which are incorporated herein by reference.

Suitable oxidizing agents for carrying out a Baeyer-Williger Oxidation include peracids such as m-chloroperbenzoic acid (hereinafter "mCPBA"), perbenzoic acid and peracetic acid. The reaction is carried out in the presence of an acid catalyst, for example, sulfonic acids such a methyl sulfonic acid, benzene sulfonic acid and p-toluene sulfonic acid. Suitable solvents include halogenated solvents such as methylene chloride, chloroform and dichloroethane.

Suitable amounts of oxidizing agent include between about 1.1 to about 2.0 equivalents with respect to the third intermediate. Suitable amounts of acid catalyst include between about 0.1% to about 10% by weight with respect to the oxidizing agent, preferably about 3–7%. Additional oxidizing agent and acid catalyst can be added if the reaction does not go to completion. Suitable concentrations of the third intermediate in the reaction mixture include between about 0.005 M to about 5.0 M, preferably between about 0.05 M to about 0.5 M. The reaction is typically performed at room temperature, but can also be carried out, for example, at temperatures ranging from about 0° C. to the about 45° C. Specific conditions for carrying out a Baeyer-Williger Oxidation on a third intermediate, specifically 2-formyl-estra-3,β17-diol dibenzyl ether (2), are provided in Example 4.

The ester group of the fourth intermediate is cleaved to form a fifth intermediate represented by Structural Formula (V):

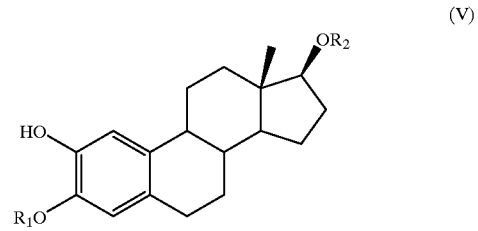

(V)

The cleavage of esters includes hydrolysis or alcoholysis of esters, which are well known in the field of chemistry. Conditions for the hydrolysis or alcoholysis of esters are described, for example, in Marvel, Org. Syn., Coll., 3:495 (1995) and Marvel, Org. Syn., Coll. 2:416 (1943), the teachings of which are incorporated herein by reference. Specific conditions for hydrolyzing the ester of a fourth chemical intermediate are provided Example 4.

"Cleaving an ester" also refers to reacting an ester R—CO—O—R' with a reducing agent suitable for reducing the ester to alcohols R—CH$_2$—OH and R'OH. Suitable reducing reagents are well known in the art and include, for example, lithium aluminum hydride, lithium borohydride and diborane. Conditions suitable for suitable for reducing an ester R—CO—O—R' to alcohols R—OH and R'OH with an ester reducing agent are also well known in the art and are disclosed, for example, in Brown et al., Aldrichimica Acta 12:3 (1979) and references cited therein, the teachings of which are incorporated herein by reference.

There are many other reactions known to the skilled artisan which are suitable for cleaving an alkyl aryl ester, such as is found in the compound represented by Structural Formula (IV) to give a compound represented by Structural Formula (V). It is to be understood that these reactions are also encompassed by the term "cleaving the ester group".

The fifth intermediate is alkylated to form a sixth intermediate represented by Structural Formula (VI):

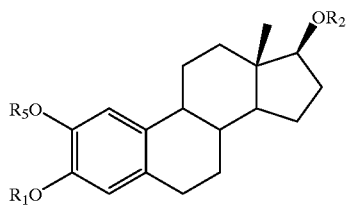

(VI)

$R_1$, $R_2$ and $R_5$ are as defined above. As used herein, "alkylation" refers to converting a phenolic group aryl—OH to the alkyl aryl ether aryl—O—$R_3$, wherein $R_3$ is as defined above. The alkylation of phenols is well known in the field of organic synthesis and can be carried out, for example, by the "Williamson Reaction". Conditions for carrying out the Williamson Reaction as well as other reactions suitable for alkylating phenolic groups are described in, for example, March, "Advanced Organic Chemistry", third edition, John Wiley & Sons, pages 342–43 (1985) and references cited therein, the teachings of which are incorporated herein by reference.

The alkylation can be carried out, for example, by reacting the fifth intermediate with an alkylating agent $R_5X$, wherein X is a leaving group such as —Br, —I, mesylate, tosylate, brosylate or other suitable sulfonate ester, triflate or —O—SO—$OCH_3$. Examples include an alkyl bromide, an alkyl iodide (e.g., methyl iodide, ethyl iodide or 2,2,2-trifluoro-iodo-ethane) or a dialkyl sulfate (e.g., dimethyl sulfate) in the presence of a suitable base (e.g., potassium hydroxide, potassium carbonate or mercury (I) oxide). Suitable amounts of alkylating agent and base range, for example, from about 1.0 equivalent to about 10.0 equivalents and from about 1.0 to about 3.0 equivalents, respectively. Additional base and alkylating agent can be added if the reaction does not go to completion.

The fifth intermediate is reacted at concentrations, for example, ranging from about 0.01 M to about 5.0 M, preferably from about 0.1 M to about 0.5 M. Suitable solvents include halogenated solvents such as methylene chloride and aprotic polar solvents such as dimethylformamide. The reaction temperature ranges, for example, from about room temperature to about 150° C.; when aprotic polar solvents are used, the reaction temperature preferably ranges from about 110° C. to about 130° C.

Specific conditions for alkylating a compound represented by Structural Formula (VI), specifically estradiol (6) and estradiol (8) in the FIGURE, are provided in Examples 5 and 6B respectively.

The protected hydroxyl groups at the three and seventeen positions in the sixth intermediate are deprotected to give a 2-alkoxy estradiol represented by Structural Formula (VII):

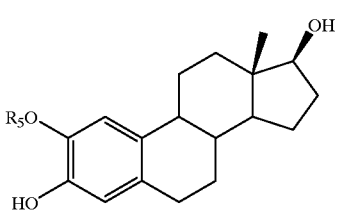

(VII)

$R_5$ is as defined above.

As discussed earlier, suitable conditions for removing phenolic protecting groups are known in the art and are described in, for example, Greene and Wuts, "Protective Groups in Organic Synthesis", John Wiley & Sons (1991). When the hydroxyl protecting groups are benzylic or substituted benzylic groups, the deprotection reaction is referred to herein as a "debenzylation". Protected hydroxyl groups can be debenzylated by hydrogenolysis over a palladium catalyst, for example Pd(OH)$_2$—C in an etheral solvent (e.g. THF, diethyl ether) or an alcoholic solvent (methanol or ethanol). Suitable pressures include from about 10 to about 120 psi, preferably from about 40–60 psi. The hydrogenation can be carried-out, for example, at temperatures from about 150° C. to about 45° C., but preferably at room temperature, and at concentrations of the sixth intermediate ranging, for example, from about 0.01 M to about 5.0 M. The reaction is continued until complete, and can be monitored by thin layer chromatography. Specific conditions for debenzylating a hydroxyl represented by Structural Formula (VI), specifically estradiols (7) and (8) in the FIGURE, are provided in Example 6.Other conditions for debenzylating a hydroxyl group are disclosed in Chapters 2 and 3 of Wuts and Greene and are within the scope of the present invention.

In another embodiment of the present invention, the sixth intermediate represented by Structural Formula (VI), can be prepared directly from a compound represented by Structural Formula (III). Specifically, bromide is nucleophilically displaced by an alkali metal alkoxide $R_5O$—$Y^+$, wherein $Y^+$ is an alkali metal cation, in the presence of a catalytic amount of copper (I) iodide. The reaction is typically carried out in an aprotic dipolar solvent such dimethylformamide. The reaction nucleophilic displacement of halides from aryl halides with nucleophilies in the presence of copper (I) iodide is well known in the art as the "Ullman Reaction". Conditions for carrying out the Ullman Reaction are described in March, "Advanced Organic Chemistry", third edition, John Wiley and Sons, pages 597–598, references cited therein, and in Vyas and Shah, Org. Syn. Coll. Vol. 3, page 836, the teachings of which are incorporated by reference. Specific conditions for carrying out this reaction are described in Example 6A.

The invention is illustrated by the following examples which are not intended to be limiting in any way.

EXEMPLIFICATION

Melting points were determined in capillary tubes on a Mel-Temp apparatus and are uncorrected. Spectra were obtained as follows: CI mass spectra on a Finnegan 4000 spectrometer; FAB mass spectra and EI mass spectra on a Kratos MS50 spectrometer; $^1H$ NMR spectra on a Bruker AC 300 spectrometer; IR spectra on a Beckman IR-33 spectrophotometer, or a Nicolet FT-IR Impact 410 spectrophotometer. Microanalyses were performed by MicroAtlantic Laboratories, Atlanta, and all values were within±0.4% of the calculated compositions.

EXAMPLE 1

3,17β-Dibenzyloxyestra-1,3,5(10)-Triene (5)

Sodium hydride (2.6 g, 65 mmol) was added in four portions to a solution of estra-3,17β-diol (3) (1, 5.0 g, 18 mmol) in anhydrous DMF (150 mL) under argon at 0° C., and the resulting mixture was stirred at 0° C. for 15 min. Benzyl bromide (12.5 mL, 105 mmol) was added, followed by tetrabutylammonium iodide (0.50 g, 1.35 mmol). Stirring was continued for 2 days at room temperature. The reaction mixture was cooled to 0° C. and 50% aqueous ethanol (20 mL) was added slowly, followed by dropwise addition of 3 N HCl (18mL) at 0° C. to 5° C. The compound was extracted into ether (3×200 mL). The ether layer was washed with water (100 mL), brine (100 mL) and dried over anhydrous sodium sulfate. Evaporation of the ether layer under reduced pressure gave a viscous oil. Trituration with hexane afforded a white solid (5.0 g, 60%), which was collected by filtration and dried under vacuum: mp 74–78° C. [Fuji et al., *J. Org. Chem.*, 44:1661–1664 (1979)., mp 81–82° C. (ethanol, acetone); Hamacher, H.; Christ, E. Potential Antineoplastics. 7th Comm: Introduction of a Nitrogen Mustard Group into the 6α-Position of Estradiol. *Arzneim. Forsch.*, 33:347–352 (1983). mp 62° C. (aq. Methanol)]; $R_f$0.334 (hexane-ethyl acetate (95:5), silica gel]; IR (KBr) 2910, 2850, 1600, 745, 685 cm$^{-1}$; $^1$H NMR (CDCL$_3$) δ 0.9 (s, 3 H), 1.05–2.45 (m, 14H), 2.83 (m, 1 H), 3.5 (t, J=8.5 Hz, 1 H), 4.57 (s, 2 H), 5.05 (s, 2 H), 6.67–6.82 (m, 2 H), 7.12–7.57 (m, 11 H). Anal. ($C_{32}H_{36}O_2$) C, H.

EXAMPLE 2
2—Bromo-3,17β-Dibenzyloxyestra-1,3,5(10)-Triene (4)

Bromine (0.58 mL, 11.3 mmol) was added by syringe to an ice-cold, stirred solution of estradiol (5) (4.5 9, 10 mmol) in an acetic acid/THF mixture (3:2, 45 mL). The resulting reaction mixture was allowed to warm to room temperature with stirring. After 1.5 h, the mixture was poured onto an ice-water mixture (200 mL), and compound was extracted with dichloromethane (3×200 mL). The combined organic layer was washed with water (200 mL), saturated aqueous sodium bicarbonate (200 mL), 10% aqueous sodium thiosulfate (150 mL), water (100 mL), brine (100 mL), and dried over anhydrous sodium sulfate. The organic layer, on evaporation under vacuum, followed by trituration with hexane-ethyl acetate mixture, gave the product (3.9 g, 75%). Only about 10% of the 4-bromo regioisomer is formed. An analytical sample was prepared by crystallization from ethyl acetate; mp 156–158° C.; IR (KBr) 2960–2840, 1600, 1590, 730–720, 685 cm$^{-1}$; $^1$H NMR (CDCL,) δ 0.9 (s, 3H), 1.10–2.40 (m, 13H), 2.75–2.85 (m, 2H), 3.5 (t, J=8.5 Hz, 1H), 4.6 (s, 2 H), 5.63 (s, 2 H), 6.67 (s, 1 H), 7.25–7.60 (m, 11 H). Anal. ($C_{32}H_{35}BrO_2$) C, H.

These results show that 2-bromo-β-estradiol dibenzyl ether (4) can be obtained in 75% yield from β-estradiol dibenzyl ether (5) with diminished formation of the 4-bromo by-product.

EXAMPLE 3
2-Formyl-3,17β-Dibenzyloxyestra-1,3,5(10)-Triene (2)

A 1.6 M solution of n-BuLi (17.5 mL) in hexanes was added dropwise by syringe under argon atmosphere at −78° C. to a solution of estradiol (4) (5.88 g, 11.2 mmol) in anhydrous THF (150 mL), and the resulting reaction mixture was stirred at −78° C. for 2 h. Anhydrous DMF (5.5 mL) was added and the stirring was continued for 1 h at −78° C. The mixture was warmed to 0° C. and stirred for 1 h, and poured onto an ice-cold solution of 3N HCl (100 mL). The aqueous layer was extracted with ether (3×300 mL). The combined organic layer was washed with 50% brine-water (100 mL), brine (150 mL), and dried over anhydrous sodium sulfate. The organic layer was filtered and evaporated under reduced pressure to afford impure estradiol (2), which was purified over a silica gel column using hexane-ethyl acetate as eluant. Appropriate fractions were combined and evaporated under reduced pressure to afford estradiol (2) (4.36 g, 82%): mp 145–147° C.; IR (KBr) 2920, 2820, 1675, 1600, 728, 685 cm$^{-1}$, $^1$H NMR (CDCl$_3$) δ 0.88 (s, 3 H), 1.1–2.5 (m, 13 H), 2.80–2.97 (m, 2 H), 3.50 (t, J=8.5 Hz, 1 H), 4.56 (s, 2 H), 5.65 (s, 2 H), 6.75 (s, 1H), 7.20–7.50 (m, 10 H), 7.78 (s, 1 H), 10.5 (s, 1 H). Anal. ($C_{34}H_{40}O_3$)C,H.

These results show that 3,17-diprotected 2-bromo-β-estradiols can be converted in high yield to 3,17-diprotected 2-formyl-β-estradiols by a halogen-metal exchange followed by quenching with dimethylformamide.

EXAMPLE 4
2—Hydroxy-3,17β-Dibenzyloxyestra-1,3,5(10)-Triene (6)

mCPBA (3.3 g, 19.1 mmol) and p-toluenesulfonic acid monohydrate (0.16 g, 0.84 mmol) were added successively to a solution of estradiol (2) (5.8 g, 12.1 mmol) in anhydrous dichloromethane (150 mL). The resulting mixture was stirred at room temperature, and the reaction was followed by TLC (dichloromethane/silica gel). After 10 h, additional amounts of mCPBA (1.0 g) and p-toluenesulfonic acid (0.040 g) were added, and stirring was continued for 5 h. The reaction mixture was diluted with dichloromethane (300 mL), and the organic layer was washed with 10% sodium sulfite solution (100 mL), water (100 mL), brine (100 mL), and dried over anhydrous sodium sulfate. The organic layer on evaporation under reduced pressure afforded 4.85 g of crude 2-formyloxy-estra-3,17 β-diol dibenzyl ether (4.85 g). This was suspended in anhydrous methanol (250 mL), four drops of conc H$_2$SO$_4$ were added, and the resulting mixture was stirred at 90° C. for 1h. The methanol was removed under reduced pressure at 50° C. and the resulting residue was dissolved in dichloromethane (400 mL). The organic layer was washed with water (100 mL), saturated sodium bicarbonate solution (100 mL), water (100 mL), and brine (100 mL), and dried over anhydrous sodium sulfate. The dichloromethane layer on evaporation under reduced pressure gave crude compound (6) (4.15 g) as a gummy solid, which on purification over a silica gel column using hexanedichloromethane mixture as an eluant provided pure estradiol (6) (3.8 g, 67%) as a white colored solid: mp 117–118° C.; $R_f$0.364 (dichloromethane, silica gel); IR (KBr) 3540, 2960–2840, 1510, 1450, 735–720, 685 cm$^{-1}$; $^1$H NMR (CDCl$_3$) δ 0.9 (s, 3 H), 1.05–2.40 (m, 1 H), 2.80 (m, 1 H), 3.50 (t, J=8.5 Hz, 1 H), 4.60 (s, 2 H), 5.08 (s, 2 H), 5.5 (s, 1 H), 6.65 (s, 1 H), 6.82 (s, 1 H), 7.20–7.50 (m, 10 H). Anal. ($C_{32}H_{36}O_3$) C, H.

EXAMPLE 5
2-(2′,2′,2′-Trifluoroethoxy)-3,17(-Dibenzyloxyestra-1,3,5(10)-Triene (7)

Powdered K$_2$CO$_3$ (1.5 g, 11 mmol) was added to a solution of estradiol (6) (4.0 g, 8.5 mmol) in anhydrous DMF (50 mL) followed by dropwise addition of CF$_3$CH$_2$I (5.0 mL, 51 mmol) at room temperature. The resulting reaction mixture was heated at 110° C. for 3 h. Additional K$_2$CO$_3$ (2.5 g) and CF$_3$CH$_2$I (6 mL) were added, and the mixture was heated again at 130° C. for 2 h. The mixture was cooled in an ice bath and poured onto ice cold 3N HCl (125 mL). The aqueous layer was extracted with ether (2×200 mL). The combined ether layer was washed with 3 N HCl (100 mL), water (100 mL), brine (100 mL), and dried over anhydrous MgSO$_4$. The ether layer was evaporated under reduced pressure and the resulting crude product on purification on a silica gel column gave estradiol (7) (4.5 g, 95%) as a colorless oil: IR (neat) 2910, 2850, 1600, 1500, 730, 690 cm$^{-1}$; $^1$H NMR (CDCl$_3$) δ 0.9 (s, 3 H), 1.1–2.4 (m, 13 H), 2.65–2.85 (m, 2 H), 3.50 (t, J=8.5 Hz, 1H), 4.40 (q, J=8.5 Hz, 2 H), 4.56 (s, 2 H), 5.05 (s, 2 H), 6.70 (s, 1 H), 6.98 (s, 1 H), 7.2–7.55 (m, 10 H). Anal. ($C_{34}H_{37}F_3O_3$) C, H.

EXAMPLE 6
2-(2′,2′,2′-Trifluoroethoxy)estra-1,3,5(10)-Trien-3,17β-Diol (9)

Pd(OH)$_2$—C(20%, 1.0 g) was added carefully under argon atmosphere to a solution of estradiol (7) (1.0 g, 1.8 mmol) in anhydrous THF (50 mL). The resulting mixture was hydrogenated at 45–50 psi on a Parr apparatus for 24 h. The catalyst was removed by filtration using a celite pad under argon atmosphere, and the pad was washed with dichloromethane (200 mL). Evaporation of the filtrate under reduced pressure, followed by purification on a silica gel column, gave compound (9) (0.5 g, 75%): mp 167–168° C.; IR (KBr) 3550, 2960–2840, 1590, 1510, 870 cm$^{-1}$; $^1$H NMR (CDCl)$_3$ δ 0.80 (s, 3 H), 1.10–2.40 (m, 13 H), 2.70–2.85 (m, 2 H), 3.75 (m, 1 H), 4.40 (q, J=8.5 Hz, 2 H), 5.35 (s, 1 H, OH), 5.5 (s, 1 H), 6.70 (s, 1 H), 6.80 (s, 1 H); MS m/z (relative intensity) 370 (100), 311 (9), 270 (8), 244 (8), 205(6). Anal. ($C_{20}H_{25}O_3$0.7 $H_2O$) C, H.

EXAMPLE 6A

2-Ethoxy-3,17β-dibenzyloxyestra-1,3,5(10)-triene(8):

To a stirred solution of sodium ethoxide (10.5 g, 154 mmol) in anhydrous ethanol (30 mL), anhydrous DMF was added under argon atmosphere and stirring was continued for 20 minutes at room temperature. To the above solution CuI (10.6 g, 56 mmol) and 2-bromocompound (4) (5.3 g, 10.0 mmol) were added successively, and the resulting mixture was stirred at 105° C. to 110° C. for 7 to 8 hours. The reaction was cooled and poured onto ice-cold water (200 mL), and followed by addition of 3 N HCl (25 mL). The insoluble material was filtered off through a celite pad and the aqueous layer was extracted with dichlomethane (300 mL×3). The combined organic layer was washed with water (200 mL), brine (200 mL), and dried over sodium sulfate. The organic layer was filtered and evaporated under reduced pressure to afford a mixture which was purified over a silica gel column using hexane:ethyl acetate as an eluent. Appropriate fractions were combined and evaporated under reduced pressure. Yield of compound (8) was 60%; mp 76° C.–77° C.; IR (KBr) 2910, 2850, 740, 685 cm$^{-1}$. $^1$H NMR (CDCl$_3$) δ 0.9 (s, 3H, —CH$_3$), 1.1–2.35 (m, 18H, —CH, —CH$_2$ & CH$_3$), 3.5 (t, 1H, —OCH), 4.10 (q, 2H, —OCH$_2$), 4.6 (s, 2H, —OCH$_2$), 5.60 (s, 2H, —OCH$_2$), 6.64 (s, 1H, Ar—H), 6.89 (s, 1H, Ar—H), 7.15–7.55 (m, 10H, Ar—H). Analysis calcd for $C_{34}H_{40}O_3$. C, 82.2;H, 8.12. Found: C, 82.51;H. 8.11. In addition to desired product (8), two minor by products 2-methoxy-3,17β-dibenzloxyestra-1,3,5(10)-triene and 2—N,N-dimethylamino-3,17β-dibenzyloxyestra-1,3,5(10)-triene were also obtained in 5% and 0.72% yield respectively.

EXAMPLE 6B

2-Ethoxyestra-1,3,5(10)-trien03,17β-diol(10)

To a solution of 2-ethoxyderivative (8) (1.1 g,2.3 mmol) in anhydrous THF (40 mL), 20% Pd (OH)$_2$—C(2.3 g) was added carefully under argon atmosphere. The resulting mixture was hydrogenated at 45–50 psi on a Parr Apparatus for four hours. The resulting mixture was monitored by TLC. After completion, the catalyst was removed via filtration using a celite pad under argon atmosphere, and pad was washed with dichlomethane (100 mL). Filtrate on evaporation under reduced pressure gave 0.8 9 of impure compound, which was purified by column chromatography. Yield>95%; mp 154° C.–156° C. [lit. 154° C.–156° C.]; [α]$_D$ +92.24° (c=0.508, CHCl$_3$){lit. [α]$_D$=+90° (c=0.5, CHCl$_3$}. IR (KBr) 3720, 3380, 2980–2840, 1580, 1510 cm$^{-1}$. $^1$H NMR (CDCl$_3$) δ 0.83 (s, 3H, —CH$_3$), 1.10–2.38 (m, 16H, —CH, CH$_3$ & —CH$_2$), 2.70–2.90 (m, 2H, —CH$_2$), 375 (m, lH, —OCH), 4.10 (q, 2H, —OCH), 5.5 (s, 1H, OH), 6.67 (s, $_1$H, Ar—H), 6.82 (s, 1H, Ar—H). Analysis calcd. For $C_{20}H_{28}O_3$. C, 75.91; H, 8.92. Found: C, 75.97;H, 8.96.

EXAMPLE 7

Tubulin Assays

Electrophoretically homogeneous tubulin was purified from bovine brain as described previously (Hamel et al., *Biochemistry* 23:4173–4184 (1984)). Determination of IC$_{50}$ values for the polymerization of purified tubulin was performed as described in D'Amato et al. *Proc. Natl. Acad. Sci. U.S.A.* 91:3964–3968 (1994). Tubulin was preincubated at 26° C. with varying compound concentrations, reaction mixtures were chilled on ice, GTP (required for the polymerization reaction) was added, and polymerization was followed at 26° C. by turbidimetry at 350 nm in Gilford recording spectrophotometers equipped with electronic temperature controllers. Four instruments were used, and two control reaction mixtures were present in each experiment. The extent of polymerization after a 20 min incubation was determined (the values for the two controls were usually within 5% of each other). IC$_{50}$ values were determined graphically. Active compounds were examined in at least three independent assays, while inactive compounds (defined as IC$_{50}$ value>40 μM) were examined in at least two independent experiments. Inhibition of colchicine binding to tubulin was performed as described previously (D. Amato et al., *Proc. Natl. Acad. Sci. U.S.A.* 91:3964–3968 (1994)). Reaction mixtures contained 1.0 μM tubulin (0.1 mg/mL), 5.0 μM [$^3$H]colchicine, and 50 μM inhibitor. Incubation was for 30 min at 37° C.

The inhibitory activities of 2-methoxy estradiol (1), 2-ethoxy estradiol (10), and 2-(2',2',2'-trifluoroethoxy) estradiol (9) on tubulin polymerization are reported in Table 1. Inhibition of tubulin polymerization was investigated using electrophoretically homogeneous tubulin from bovine brain. 2-ethoxy estradiol (10) was over three times more active than 2-methoxy estradiol (1).

EXAMPLE 8

Activity of 2-alkoxy Estradiols an Analogs Thereof in the National Cancer Institute Anticancer Screen The effects of the analogs on cancer cell growth was investigated in the National Cancer Institute (NCI) Developmental Therapeutics Program's in vitro panel of approximately 55 cell lines (Grever et al., *Seminars in Oncology* 19:622 (1992), Alley et al., *Cancer Research* 48:589 (1988) and Montes et al., *J. National Cancer Institute* 83:757 (1991)). Representative results are listed in Table 1 for HOP-62 non-small-cell lung cancer cells, HCT-116 colon cancer cells, SF-539 central nervous system (CNS) cancer cells, UACC-62 melanoma cells, OVCAR ovarian cancer cells, SN12—C renal cancer cells, DU-145 prostate cancer cells, and MDA-MB-435 breast cancer cells. 2-Ethoxy estradiol (10) was more active against all the cell lines listed in Table 1 than 2-methoxy estradiol (1).

TABLE 1

Cytotoxicities and Antitubulin Activities of
2-Methoxyestradiol and Analog cytotoxicity ($GI_{50}$ in $\mu M$)[a]

| No. | Lung HOP-62 | Colon HCT-116 | CNS SF-539 | Melanoma UACC-62 | Ovarian OVCAR | Renal SN12-C | Prostate DU-145 | Breast MDA-MB-435 | MGM[b] | Inhibn of Tubulin Polymn $IC_{50}$ ($IC_{50}$ $\mu M$) |
|---|---|---|---|---|---|---|---|---|---|---|
| 1 | 0.70 | 0.47 | 0.32 | 0.36 | 0.21 | 0.95 | 1.8 | 0.080 | 1.30 | 2.9 ± 0.6 |
| 59 | 11.6 | 3.22 | 1.38 | 2.32 | 0.46 | 4.46 | 7.05 | 0.28 | 2.63 | 1.7 |
| 14 | 0.018 | 0.026 | 0.014 | 0.016 | 0.016 | 0.039 | 0.065 | <0.01 | 0.076 | 0.91 ± 0.5 |

[a]The cytotoxicity $GI_{50}$ values are the concentrations corresponding to 50% growth inhibition.
[b]Mean graph midpoint for all human cancer cell lines (approximately 55) tested.

EQUIVALENTS

Those skilled in the art will be able to recognize, or be able to ascertain using no more than routine experimentation, many equivalents to the specific embodiments of the invention described herein. Such equivalents are intended to be encompassed by the following claims.

What is claimed is:

1. A method of preparing a compound represented by the following structural formula:

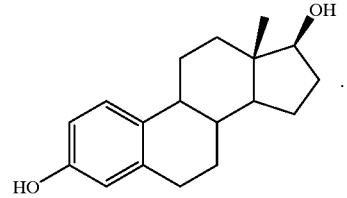

comprising reacting a precursor compound represented by the following structural formula:

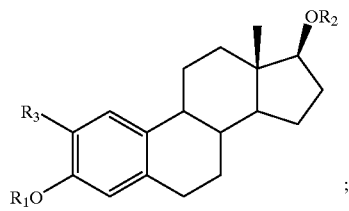

with reagents consisting essentially of Br2 or I2 and an aliphatic organic acid in an etheral solvent, wherein $R_1$ and $R_2$ are each independently a benzyl or substituted benzyl group: and $R_3$ is —Br or —I.

2. The method of claime 1, wherein the precursor compound is reacted with $Br_2$ and an aliphatic organic acid is an etheral solvent and $R_3$ is —Br.

3. The method of claim 2 wherein the aliphatic organic acid is a C1–C5 aliphatic carboxylic acid.

4. The method of claim 3 wherein the aliphatic organic acid is acetic acid and $R_1$ and $R_3$ are benzyl groups.

5. The method of claim 3 wherein the precursor compound is prepared by benzylating a compound represented by the following structural formula:

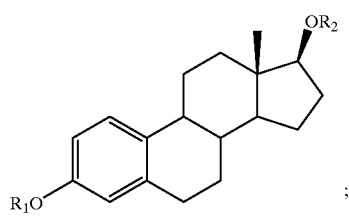

* * * * *

UNITED STATES PATENT AND TRADEMARK OFFICE
CERTIFICATE OF CORRECTION

PATENT NO. : 6,054,598
DATED : April 25, 2000
INVENTOR(S) : Yesh Sachdeva, et. al.

It is certified that error appears in the above-indentified patent and that said Letters Patent is hereby corrected as shown below:

At Claim 4, line 2, delete "$R_1$ and $R_3$" and substitute therefor --$R_1$ and $R_2$--.

Signed and Sealed this

Twentieth Day of March, 2001

*Attest:*

NICHOLAS P. GODICI

*Attesting Officer*     *Acting Director of the United States Patent and Trademark Office*